US009351827B2

United States Patent
Toner et al.

(10) Patent No.: US 9,351,827 B2
(45) Date of Patent: May 31, 2016

(54) LENS DRIVER FOR VARIABLE-OPTIC ELECTRONIC OPHTHALMIC LENS

(71) Applicant: Johnson & Johnson Vision Care, Inc., Jacksonville, FL (US)

(72) Inventors: Adam Toner, Jacksonville, FL (US); Daniel B. Otts, Fruit Cove, FL (US); Scott Robert Humphreys, Greensboro, NC (US); William Chester Neeley, Melbourne, FL (US); Randall Braxton Pugh, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 590 days.

(21) Appl. No.: 13/798,295

(22) Filed: Mar. 13, 2013

(65) Prior Publication Data
US 2013/0258275 A1 Oct. 3, 2013

Related U.S. Application Data

(60) Provisional application No. 61/619,524, filed on Apr. 3, 2012.

(51) Int. Cl.
*G02C 7/04* (2006.01)
*A61F 2/16* (2006.01)
*G02C 7/08* (2006.01)

(52) U.S. Cl.
CPC .............. *A61F 2/1627* (2013.01); *G02C 7/04* (2013.01); *G02C 7/083* (2013.01)

(58) Field of Classification Search
CPC .......... G02C 7/04–7/049; G02C 7/081; G02C 7/083; G02C 7/085; B29D 11/00807; B29D 11/00817; B29D 11/00826; B29D 11/00951; B29D 11/00961

USPC ............. 351/159.01, 159.02, 159.03–159.21, 351/159.39–159.4
See application file for complete search history.

(56) References Cited

U.S. PATENT DOCUMENTS

| | | | |
|---|---|---|---|
| 2007/0260307 A1 | 11/2007 | Azar | |
| 2010/0076553 A1 | 3/2010 | Pugh | |
| 2010/0110372 A1* | 5/2010 | Pugh | B29D 11/00009 351/159.75 |

FOREIGN PATENT DOCUMENTS

| | | |
|---|---|---|
| EP | 1760515 A2 | 7/2007 |
| WO | WO 2010/051225 A9 | 6/2010 |

(Continued)

OTHER PUBLICATIONS

European Search Report completed Jul. 19, 2013 for corresponding Patent Application No. EP13162192.

(Continued)

*Primary Examiner* — Ricky Mack
*Assistant Examiner* — Robert E Tallman
(74) *Attorney, Agent, or Firm* — Carl J. Evens

(57) ABSTRACT

A lens driver or lens driver circuitry for an ophthalmic apparatus comprising an electronic system which actuates a variable-focus optic is disclosed herein. The lens driver is part of an electronic system incorporated into the ophthalmic apparatus. The electronic system includes one or more batteries or other power sources, power management circuitry, one or more sensors, clock generation circuitry, control algorithms and circuitry, and lens driver circuitry. The lens driver circuitry includes one or more power sources, one or more high voltage generators and one or more switching circuits.

13 Claims, 10 Drawing Sheets

(56) References Cited

FOREIGN PATENT DOCUMENTS

| WO | WO 2011/163080 | * | 12/2011 | ............ A61F 2/1624 |
| WO | WO 2011/163080 | A1 | 12/2011 | |

OTHER PUBLICATIONS

Written Opinion issued by the Hungarian Intellectual Property Office dated May 22, 2014, for Application No. 201302104-3.

* cited by examiner

LENS DRIVER FOR VARIABLE-OPTIC ELECTRONIC OPHTHALMIC LENS

CROSS REFERENCE TO RELATED APPLICATIONS

This patent application claims the benefit of U.S. Provisional Patent Application No. 61/619,524, filed Apr. 3, 2012.

BACKGROUND OF THE INVENTION

1. Field of the Invention

The present invention relates to a variable-optic powered or electronic ophthalmic lens, and more particularly to electronic circuits for powering a variable-optic electronic ophthalmic lens.

2. Discussion of the Related Art

As electronic devices continue to be miniaturized, it is becoming increasingly more likely to create wearable or embeddable microelectronic devices for a variety of uses. Such uses may include monitoring aspects of body chemistry, administering controlled dosages of medications or therapeutic agents via various mechanisms, including automatically, in response to measurements, or in response to external control signals, and augmenting the performance of organs or tissues. Examples of such devices include glucose infusion pumps, pacemakers, defibrillators, ventricular assist devices and neurostimulators. A new, particularly useful field of application is in ophthalmic wearable lenses and contact lenses. For example, a wearable lens may incorporate a lens assembly having an electronically adjustable focus to augment or enhance performance of the eye. In another example, either with or without adjustable focus, a wearable contact lens may incorporate electronic sensors to detect concentrations of particular chemicals in the precorneal (tear) film. The use of embedded electronics in a lens assembly introduces a potential requirement for communication with the electronics, for a method of powering and/or re-energizing the electronics, for interconnecting the electronics, for internal and external sensing and/or monitoring, and for control of the electronics and the overall function of the lens.

The human eye has the ability to discern millions of colors, the ability to adjust easily to shifting light conditions, and transmit signals or information to the brain at a rate exceeding that of a high speed internet connection. Lenses, such as contact lenses and intraocular lenses, currently are utilized to correct vision defects such as myopia, hyperopia and astigmatism. However, properly designed lenses incorporating additional components may be utilized to enhance vision as well as to correct vision defects.

Conventional contact lenses are polymeric structures with specific shapes to correct various vision problems as briefly set forth above. To achieve enhanced functionality, various circuits and components have to be integrated into these polymeric structures. For example, control circuits, microprocessors, communication devices, power supplies, sensors, actuators, light emitting diodes, and miniature antennas may be integrated into contact lenses via custom built optoelectronic components to not only correct vision, but to enhance vision as well as provide additional functionality as is explained herein. Electronic and/or powered contract lenses may be designed to provide enhanced vision via zoom-in and zoom-out capabilities or just simply modifying the refractive capabilities of the lenses. Electronic and/or powered contact lenses may be designed to enhance color and resolution, to display textural information, to translate speech into captions in real time, to offer visual cues from a navigation system, to provide image processing and internet access. The lenses may be designed to allow the wearer to see in low light conditions. The properly designed electronics and/or arrangement of electronics on lenses may allow for projecting an image onto the retina, for example, without a variable focus optic lens, provide novelty image displays and even provide wakeup alerts. Alternately, or in addition to any of these functions or similar functions, the contact lenses may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured lens may incorporate sensors for monitoring cholesterol, sodium and potassium levels as well as other biological markers. This coupled with a wireless data transmitter could allow a physician to have almost immediate access to a patient's blood chemistry without the need for the patient to waste time getting to a laboratory and having blood drawn. In addition, sensors built into the lenses may be utilized to detect light incident on the eye to compensate for ambient light conditions or for use in determining blink patterns.

The proper combination of devices could yield potentially unlimited functionality; however, there are a number of difficulties associated with the incorporation of extra components on a piece of optical grade polymer. In general, it is difficult to manufacture such components directly on the lens for a number of reasons, as well as mounting and interconnecting planar devices on a non-planar surface. It is also difficult to manufacture to scale. The components to be placed on or in the lens need to be miniaturized and integrated onto just 1.5 square centimeters of a transparent polymer while protecting the components from the liquid environment on the eye. It is also difficult to make a contact lens comfortable and safe for the wearer with the added thickness of additional components.

Given the area and volume constraints of an ophthalmic device such as a contact lens, and the environment in which it is to be utilized, the physical realization of the device must overcome a number of problems, including mounting and interconnecting a number of electronic components on a non-planar surface, the bulk of which comprises optic plastic. Accordingly, there exists a need for providing a mechanically and electrically robust electronic contact lens.

As these are powered lenses, energy or more particularly current consumption to run the electronics is a concern given battery technology on the scale for an ophthalmic lens. In addition to normal current consumption, powered devices or systems of this nature generally require standby current reserves, precise voltage control and switching capabilities to ensure operation over a potentially wide range of operating parameters, and burst consumption, for example, up to eighteen (18) hours on a single charge, after potentially remaining idle for years.

Vision correction, and potentially vision enhancement, is typically achieved in spectacle lenses, contact lenses, intraocular lenses (IOL's) and other ophthalmic devices through static optics. For example, spectacle lenses or contact lenses to treat myopia (nearsightedness) comprise lenses with spherical power to correct focus onto the retina caused by defects in the cornea and/or lens. Bifocal corrective lenses may contain an inset lens of a different power than the main lens. More advanced designs use gradient, zone, or other schemes to vary corrective power over the lens. However, because these lenses are optically static, they do not match the human eye's natural response which is a variable-focus action accomplished by varying the optical power of the eye's crystalline lens. In presbyopic individuals, the eye's natural ability to accommodate with different focal lengths is greatly reduced leading to a loss of function and annoyance. Recent advancements in the field have included spectacle lenses and even IOL's with some dynamic accommodation, for example, electronic spectacle lenses or IOL's connected to the eye's zonules to achieve a limited amount of optical power change. These existing systems are limited by only covering a small range of add power, perhaps only +1 diopter, requiring spectacle lenses to be worn, requiring surgery to implant an IOL, and other drawbacks.

There are several types of electronically variable lens technologies, including liquid crystal, electro-active polymer, electro-mechanical, variable fluid, and liquid meniscus lenses. Such electronically variable lenses require an actuator, and an electronic device to alter the focal length of the lens. For example, in a liquid meniscus or electro-active polymer lens, an applied voltage and/or current from an actuator modulates physical parameters of the lens to vary the focal length. Both variable lenses and their actuators, also known as lens drivers, are commercially available for various applications such as smartphone cameras and industrial applications. Suitable lenses and actuators do not exist for ophthalmic devices such as contact lenses and IOL's.

Electrical or powered lenses typically require higher voltage than what is immediately available from a battery. For example, a powered lens may require sixty (60) volts to reach the maximum change of focal length but typical batteries output less than four (4) volts. Typical lens drivers include a voltage multiplier circuit to achieve high output voltage from a low-voltage source, many designs of which are known in the art. A voltage multiplier is essentially a voltage and current conversion device, similar in principal to that of an electric transformer with mismatched primary-to-secondary ratios. Whereas a transformer operates on alternating current, a voltage multiplier operates from a direct current (DC) source such as a battery. A voltage multiplier may comprise a charge pump, a circuit type widely known in the electronics art.

Lens drivers which are presently available have many disadvantages which make them unsuitable for use in ophthalmic devices such as contact lenses and IOL's. Current consumption of typical lens drivers is on the order of approximately one (1) to more than one hundred (100) milliamps. While this is acceptable current consumption for a robotic manufacturing system with access to main line power or even a camera or smartphone with a relatively large battery, it is far too much current for a power source in an ophthalmic device. Such power sources, implemented as batteries, energy harvesters, and/or capacitors, are typically limited to current of perhaps thirty (30) microamps or less. Both the active current consumption, the current drawn by the lens driver when activating the powered lens, and the standby current consumption, the current drawn when the lens driver is not driving the powered lens, are critical parameters for an ophthalmic device.

Typical electronically variable lenses and their lens drivers are designed for applications and not optimized for ophthalmic device usage. For example, some lenses are continuously variable over a range of focal lengths from millimeters to infinity, some thirty (30) or more diopters. Commercial lenses and drivers must change focal length very quickly, perhaps within less than one hundred (100) milliseconds. Ophthalmic lenses may only need to change focus in one (1) or two (2) seconds, the time typically required for the natural eye to change focal distance, as is known in the art. Typical lens and driver systems intended for commercial and manufacturing applications must last for many years in operation and undergo wide changes in focal length many times per day. In contrast, some ophthalmic devices such as contact lenses may be disposable and only used for eighteen (18) hours.

Typical lens drivers are implemented with discrete electronics or integrated circuits (IC's). Even when implemented as IC's, lens drivers may require external components such as capacitors, and the physical die size of the lens driver may be two (2) square millimeters or more at a thickness of hundreds of microns and thus still a challenge.

Electrically variable lenses are typically activated with a voltage of ten (10) to sixty (60) volts. Thus, lens drivers for these devices must output a high voltage sufficient to activate the powered lens. Lens drivers may be programmable to change the output voltage thereby modulating the optical power of the powered lens.

Due to requirements for speed, reliability, and precise modulation of optical power over a large range of focal distances, typical lens drivers for liquid meniscus lenses utilize an alternating current (AC) driver. Such an AC driver rapidly switches the bias applied to the lens between positive and negative, perhaps at a one kilohertz (1 kHz) rate. This drive method provides benefits for existing commercial applications, but also greatly increases current consumption from the alternative direct current (DC) drive method. The liquid meniscus lens may be modeled as a capacitor, and as such the energy required to charge the capacitor is $\frac{1}{2} \times C \times V^2$ where C is the lens capacitance and V is the applied voltage. Liquid lens capacitance is approximately two hundred picofarads (200 pF). It is apparent that a large amount of power is provided and consumed by a typical high-voltage lens driver since the lens capacitance must be charged at a fast rate.

Accordingly, there exists a need for a lens driver for a powered ophthalmic lens that is optimized for low cost, long term reliable service, safety, size, and speed while providing the requisite power to drive a variable-focus optic.

SUMMARY OF THE INVENTION

The lens driver, including the electronic circuitry for powering a variable-focus optic electronic ophthalmic lens, of the present invention overcomes the disadvantages associated with the prior art as briefly set forth above.

In accordance with one exemplary embodiment, the present invention is directed to an ophthalmic apparatus. The ophthalmic apparatus comprises an ophthalmic device configured for use in at least one of in or on the eye, an electronic system incorporated into the ophthalmic device, the electronic system comprising a control system, at least one lens actuator, and a power system, including one or more power sources, the electronic system being configured for low power consumption, and an optic element incorporated into the ophthalmic device, the optic element having an electronically controlled focal length configurable for at least one of vision correction and vision enhancement, the optic element being operatively associated with the electronic system.

The present invention relates to a powered contact lens comprising an electronic system which performs any number of functions, including actuating a variable-focus optic. The electronic system includes one or more batteries or other power sources, power management circuitry, one or more sensors, clock generation circuitry, control circuitry implementing suitable control algorithms, and lens driver circuitry.

The lens actuator or lens driver circuitry generates the appropriate bias to actuate a variable-focus optic. It is activated by the system controller, control system, or control circuitry, receives current from the power management circuitry, and receives a clock signal from the clock generation circuitry. The lens actuator or lens driver circuitry comprises one or more power sources, one or more bias generators and one or more switching circuits. The lens driver circuitry converts battery-level voltage to a bias appropriate to actuate the variable-focus lens. It also includes circuitry to switch bias to the variable-focus lens, for example, ground, high voltage, polarity reversal, and floating.

In one exemplary embodiment, the variable-focus optic is an electrowetting device which requires a high voltage to change focus. The lens driver for such a variable-focus optic converts the battery-level voltage to a high-voltage bias, for example, a 25 V output from a 2 V input. In another exemplary embodiment, the variable-focus optic is an electro-mechanical or electro-fluid device. The lens driver for such a variable-focus optic may be substantially different from that required for an electrowetting device, for example, requiring a specific driving waveform and feedback of the lens or optic state. However, the function in the ophthalmic device is the same; namely, electronically controlling the focal length of a variable-focus optic of a lens. In yet another exemplary embodiment, the variable-focus optic may comprise a liquid crystal device requiring a current-mode bias.

The lens driver circuitry of the present invention offers safe, low cost, long term, reliable power in a package sized for utilization on or in an ophthalmic device, such as a contact lens, without significant impact on comfort or wearability.

To reduce current consumption, several techniques in accordance with the present invention are used which are applicable to a lens driver for an ophthalmic device. Current is reduced by carefully matching the requirements of the lens driver to the variable-focus optic of the powered lens, with the variable-focus optic of the powered lens requirements matched to those of an ophthalmic device. For example, to avoid switching losses for a liquid meniscus lens, a DC drive is used instead of an AC drive. This is possible because, in some exemplary embodiments, continuously variable focus is not needed or is substantially different than the requirements for existing lens drivers. Add power may be simply plano (0 add power) and +3 optical power. Further, the design of a specific liquid meniscus lens for an ophthalmic device reduces or eliminates the need for polarity toggling. In some exemplary embodiments, the lens driver's output is unregulated and not part of a control loop. While tight regulation of the lens driver output may be required for applications covering a wide range of focal lengths, tight regulation is not necessarily required for all ophthalmic applications. The design of the lens may allow a wide range of driver voltages to accomplish the desired change in focal length. As would be appreciated by one skilled in the art, removal of the feedback system greatly simplifies the lens driver with corresponding improvements in die size and current consumption.

Current consumption is further reduced by carefully designing the lens driver for the ophthalmic application. Active current is reduced to approximately three (3) microamps. Standby and storage current is reduced to nanoamps or picoamps. This accomplished through techniques which are known in the art as well as innovative new techniques as described in greater detail herein.

Designing the lens driver together with the lens for an ophthalmic application permits additional improvements in the lens driver. The activation voltage of the variable-focus optic of the powered lens may be reduced, with a corresponding reduction in the output voltage requirements of the lens driver, and the lens driver's current and size. The capacitance and resistance of the variable-focus optic of the powered lens may be optimized, thereby requiring less current from the lens driver. Again, this reduces the lens driver's size and current consumption.

Size and packaging are of critical importance to the suitability of a lens driver for an ophthalmic application. As such, the integration, layout, and interconnects are designed particularly for use in ophthalmics. All components of the lens driver are integrated onto one silicon integrated circuit or IC, eliminating the need for external components such as discrete surface-mount capacitors. Die size is reduced through various techniques. Interconnects are added in wafer post-processing and designed specifically for an ophthalmic application. Die are thinned, perhaps to thirty (30) to one hundred (100) microns.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
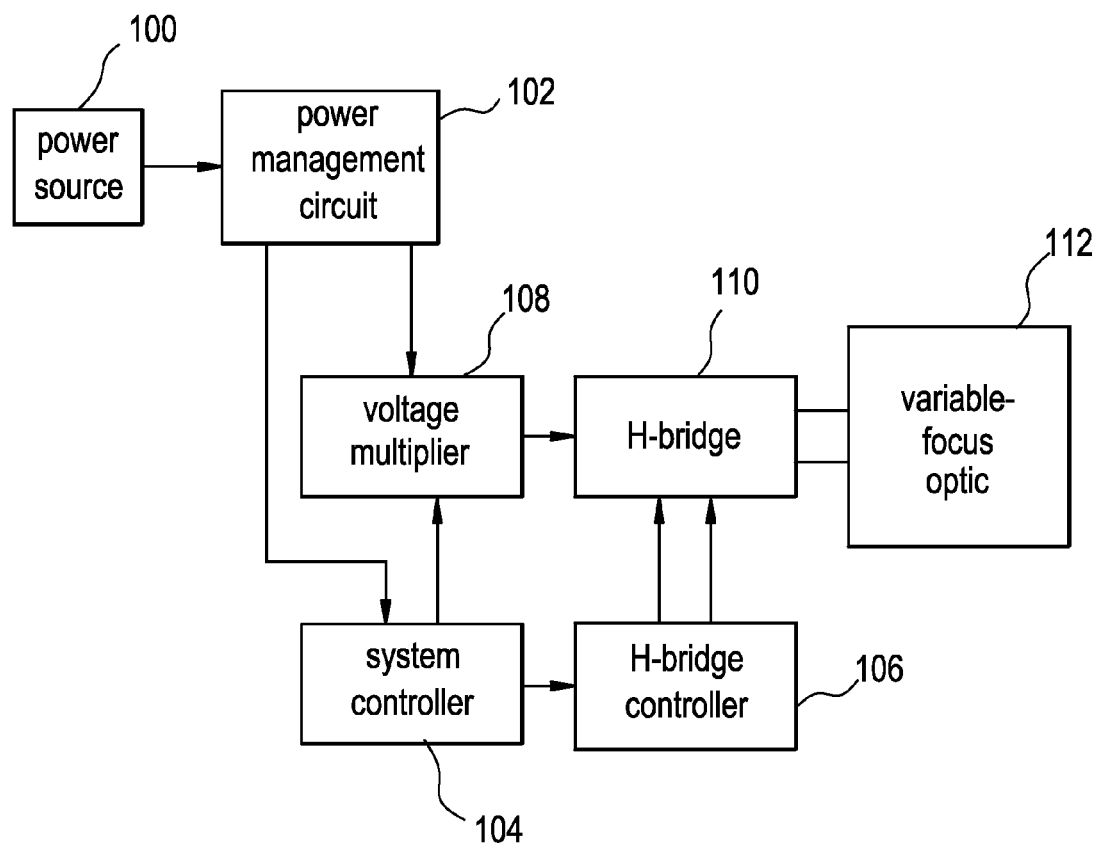
FIG. 1 is a block diagram representation of an exemplary variable-focus lens system in accordance with the present invention.

Conventional contact lenses are polymeric structures with specific shapes to correct various vision problems as briefly set forth above. To achieve enhanced functionality, various circuits and components have to be integrated into these polymeric structures. For example, control circuits, microprocessors, communication devices, power supplies, sensors, actuators, light emitting diodes, and miniature antennas may be integrated into contact lenses via custom built optoelectronic components to not only correct vision, but to enhance vision as well as provide additional functionality as is explained herein. Electronic and/or powered contract lenses may be designed to provide enhanced vision via zoom-in and zoom-out capabilities or just simply modifying the refractive capabilities of the lenses. Electronic and/or powered contact lenses may be designed to enhance color and resolution, to display textural information, to translate speech into captions in real time, to offer visual cues from a navigation system, to provide image processing and internet access. The lenses may be designed to allow the wearer to see in low light conditions. The properly designed electronics and/or arrangement of electronics on lenses may allow for projecting an image onto the retina, for example, without a variable focus optic lens, provide novelty image displays and even provide wakeup alerts. Alternately, or in addition to any of these functions or similar functions, the contact lenses may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured lens may incorporate sensors for monitoring cholesterol, sodium and potassium levels as well as other biological markers. This coupled with a wireless data transmitter could allow a physician to have almost immediate access to a patient's blood chemistry without the need for the patient to waste time getting to a laboratory and having blood drawn. In addition, sensors built into the lenses may be utilized to detect light incident on the eye to compensate for ambient light conditions or for use in determining blink patterns.

The powered or electronic contact lens of the present invention comprises the necessary elements to correct and/or enhance the vision of patients with one or more of the above described vision defects or otherwise perform a useful ophthalmic function. In addition, they may be utilized simply to enhance normal vision or provide a wide variety of functionality as described above. The electronic contact lens may comprise a variable-focus optic lens, an assembled front optic embedded into a contact lens or just simply embedding electronics without a lens for any suitable functionality. The electronic lens of the present invention may be incorporated into any number of contact lenses as described above. In addition, intraocular lenses may also incorporate the various components and functionality described herein. However, for ease of explanation, the disclosure will focus on an electronic contact lens to correct vision defects intended for single-use daily disposability.

The present invention is directed to a powered ophthalmic device or powered contact lens comprising an electronic system, which actuates a variable-focus optic or any other device or devices configured to implement any number of numerous functions that may be performed. The electronic system includes one or more batteries or other power sources, power management circuitry, one or more sensors, clock generation circuitry, control circuitry implementing suitable control algorithms, and lens driver circuitry. The complexity of these components may vary depending on the required or desired functionality of the powered or electronic lens.

It is important to note that the control circuitry, system controller or control system may receive any number of inputs for controlling a powered or electronic ophthalmic lens, for example, a contact lens comprising a variable power optic element or variable-focus optic for zooming in on or focusing on distant objects and zooming out on or focusing on close objects.

A control system comprises one or more devices configured to manage, command, direct and/or regulate the actions of other devices and/or systems. While there are a number of different types of control systems, they generally fall into two classes or types; namely, logic or sequential control systems and feedback or linear control systems. In a logic or sequential control system, command signals are output which triggers a series of actuators in a predetermined sequence to perform one or more tasks. In a feedback control system, a control loop, including one or more sensors, control algorithms, and actuators is configured to regulate a variable at a set point or reference value. In any feedback control system, one needs to know what the system is to do, to know how well the system is performing, and to use the performance information to correct and control the system.

The components of the basic feedback control system may be described as follows. The control system comprises the system or plant to be controlled and is configured to receive an input and provide an output. The output of the plant is input to a sensor which measures one or more parameters of the plant and provides a feedback signal. The feedback signal is then subtracted, via a comparator or other suitable means, from the input signal to generate an error signal. The error signal is then input to a controller which outputs a signal to the plant thereby causing the plant to implement the desired action. Essentially, the feedback from the sensor attempts to account for all of the complexities of the entire system and produces an output that is the desired result for a given input. All control systems are designed within the confines of certain control laws and typically represent tradeoffs in various aspects, including speed and accuracy. Although this description is overly simplified and described in terms of hardware, it provides the basis for feedback control systems which may be implemented in hardware, software or any combination thereof.

Feedback control systems may be further classified as proportional controllers, integral controllers, derivative controllers or combinations thereof. In a proportional controller, the control action is proportional to the error. In an integral controller, the actuating signal or input to the plant is proportional to the integral of the error. In a derivative controller, the output of the process is proportional to the rate at which the input changes. Each type of controller offers its own advantage as is known in the control art. For example, a steady state error should be achieved when utilizing an integral controller.

A sequential controller, as set forth above, is one in which a series of actions need to occur in a specific order. These actions may be quite complex, because all of the conditions of the overall process must be known. Sequential controllers generally comprise logic systems to sequence commands for controlling electrical and/or mechanical actions. Programmable logic controllers and microcontrollers may be programmed for sequential control.

Throughout the specification the term ophthalmic device is utilized. In general terms, an ophthalmic device may include contact lenses, intraocular lenses, spectacle lenses and punctal plugs. However, in accordance with the present invention, an ophthalmic device is one for vision correction and/or enhancement and preferably includes at least one of spectacle lenses, contact lenses and intraocular lenses. An intraocular lens or IOL is a lens that is implanted in the eye and replaces the crystalline lens. It may be utilized for individuals with cataracts or simply to treat various refractive errors. An IOL typically comprises a small plastic lens with plastic side struts called haptics to hold the lens in position within the capsular bag in the eye. Any of the electronics and/or components described herein may be incorporated into IOLs in a manner similar to that of contact lenses. A punctal plug or occluder is an ophthalmic device for insertion into a punctum of an eye in order to treat one or more disease states, for example, chronic dry eye. While the present invention may be utilized in any of these devices, in preferred exemplary embodiments, the present invention is utilized in contact lenses or intraocular lenses.

The present invention is directed to a powered ophthalmic lens or powered contact lens comprising an electronic system, which actuates a variable-focus optic or any other device or devices configured to implement any number of numerous functions that may be performed. The electronic system includes one or more batteries or other power sources, power management circuitry, one or more sensors, clock generation circuitry, control circuitry implementing suitable control algorithms, and lens driver circuitry. The complexity of these components may vary depending on the required or desired functionality of the lens.

The lens driver circuitry generates the appropriate bias to actuate a variable-focus lens. It is activated by the system controller, control system or control circuitry, receives current from the power management circuitry, and receives a clock signal from the clock generation circuitry. The lens driver circuitry comprises one or more power sources, one or more bias generators and one or more switching circuits. The lens driver circuitry converts battery-level voltage to a bias appropriate to actuate the variable-focus lens. It also includes circuitry to switch bias to the lens, for example, ground, high voltage, polarity reversal, and floating.

As set forth above, the present invention relates to an ophthalmic device such as a contact lens comprising a number of components, with the lens driver being one of these components. The proper combination of devices could yield potentially unlimited functionality; however, there are a number of difficulties associated with the incorporation of extra components on a piece of optical-grade polymer that makes up the contact lens. In general, it is difficult to manufacture such components directly on the lens for a number of reasons, as well as mounting and interconnecting planar devices on a non-planar surface. It is also difficult to manufacture to scale and form. The components to be placed on or in the lens need to be miniaturized and integrated onto just 1.5 square centimeters of a transparent polymer, or more particularly, seventeen (17) square millimeters, while protecting the components from the liquid environment on the eye. It is also difficult to make a contact lens comfortable and safe for the wearer with the added thickness of additional components.

In addition to the size requirements set forth herein, electronic devices incorporated into a contact lens have to be robust and safe for use in an essentially aqueous environment. Tears have a pH of about 7.4 and are about 98.2 percent water and 1.8 percent solids, including electrolytes such as sodium, potassium, calcium, magnesium, and chlorides. This is a somewhat harsh environment in which to introduce electronics. Also, contact lenses are generally designed to be worn for at least four hours and preferably longer than eight hours. Electronic components require energy. This energy may be supplied from any number of sources, including built-in batteries. Since batteries and other potential energy sources have limited potential at these sizes, all electronic components, including the lens driver, are preferably designed to consume as little power as possible so that the contact lenses may be worn for a given period of time even after sitting idle for a given period of time (shelf life). Finally, all components in an electronic contact lens have to be biocompatible and safe. Accordingly, all electronics incorporated into the contact lens have to meet all of the above design parameters; namely, size, survivability in an aqueous solution, power consumption and safety. The lens driver of the present invention meets all of these requirements.

Prior to delving into the detailed description of the present invention, it is important to note that there are many alternate exemplary embodiments of variable-focus optics. For example, the variable-focus optic may be implemented utilizing liquid crystal technology, electro-active polymer technology, variable fluid technology and liquid meniscus technology. In the following detailed description, the variable-focus optic comprises a liquid meniscus lens. The term liquid meniscus and electrowetting as set forth herein are utilized interchangeably in this specification. In order to better understand the description of exemplary embodiments of the present invention, a general overview of a liquid meniscus lens is given. A typical liquid lens comprises a cell that includes two immiscible liquids. One liquid is insulating and non-polar while the second liquid is typically a conducting water solution, such as a saline solution. Both liquids are transparent with different indexes of refraction. Preferably, both liquids have the same density such that gravity has minimal impact on lens operation. The insulating liquid is configured in the shape of a drop and placed in contact with a thin insulating window which is hydrophobic so that the insulating liquid will sit upon it. A transparent electrode is positioned on the external side of this window. The application of a voltage between the electrode and the conducting liquid favors the wettability of the surface of this same liquid thereby deforming the interface and changing the shape of the insulating liquid drop, thereby changing the focal length of the lens. This is a high level description and not intended to be construed as the specific optic element of the present invention.

In one exemplary embodiment, the variable-focus optic is an electrowetting device which requires a high voltage to change focus. The lens driver for such a variable-focus optic converts the battery-level voltage to a high-voltage bias, for example, a 25 V output from a 2 V input. In another exemplary embodiment, the variable-focus optic is an electro-mechanical or electro-fluid device. The lens driver for such a variable-focus optic may be substantially different from that required for an electrowetting device, for example, requiring a specific driving waveform and feedback of the lens state. However, the function in the ophthalmic device is the same; namely, electronically controlling the focal length of a lens. In yet another exemplary embodiment, the variable-focus optic may comprise a liquid crystal device requiring a current-mode bias.

An electrowetting lens possesses a certain amount of capacitance which arises from the physical construction of the lens. A conductive saline phase is connected to one electrical contact of the lens. A dielectric separates this conductive saline phase from an electrode which connects to the second electrical terminal of the lens. Thus, a capacitance arises between the two terminals due to the presence of the dielectric. In order to actuate the electrowetting lens, the capacitance must be charged until the terminal voltage exceeds the threshold of focal change activation. As such, the capacitance of the electrowetting lens is of critical importance to the design of the lens driver. As is known to those skilled in the art, design parameters of a lens driver may be optimized to account for the lens load and expected performance requirements. For example, with a charge pump lens driver creating a high voltage to actuate an electrowetting lens, an increase in one or more of clock frequency and capacitor size allows the charge pump to supply more current. Also as known in the art, an increase in current sourcing capability allows a capacitor to be charged faster. As such, the clock frequency and capacitor sizes of the lens driver may be optimized for electrical efficiency and actuation time for a variable-focus lens. Similar design connections exist for other electrically variable lenses and the corresponding lens drivers.

Referring now to FIG. 1, there is illustrated an exemplary embodiment of a variable-focus electronic ophthalmic lens system comprising a power source 100, a power management circuit 102, a system controller 104, an H-bridge-controller 106, a voltage multiplier 108, an H-bridge 110 and a variable-focus optic 112. The variable-focus optic 112 may be a liquid lens that changes focal properties, e.g. focal length, in response to an activation voltage applied across two electrical terminals of the lens. As set forth above, any suitable technology may be utilized. The two terminals may correspond to a front-side and a back-side terminal of the optic 112. The activation voltage may be significantly higher than voltages available from the power source, for example, twenty-five (25) volts for full lens activation and a battery providing only two (2) volts. The power source 100 may be a battery, a capacitor or similar device providing stored charge at a usable working voltage. In some exemplary embodiments, the power source 100 may be an inductive power coupling to an external power supply. The power management circuit 102 may comprise one or more voltage regulators, voltage or current references, and switches to selectively enable power supplied to other components in the electronic lens system. The system controller 104 comprises a digital control system implemented as either a microcontroller running software, or in digital logic, such as a state machine and may further comprise an oscillator for generating a periodic timing signal for the control system. The system controller 104 provides control signals to the voltage multiplier 108 and to the H-bridge controller 106 based on an internal algorithm or under external control by a user (interface not shown). The voltage multiplier 108 receives current at a low working voltage from the power source 100 and generates a high output voltage at or above the activation voltage of the variable-focus optic 112, i.e. sufficient to change the state of the variable-focus optic 112. The voltage multiplier 108 may further comprise an oscillator or receive a clock signal from the system controller 104. In the present exemplary embodiment, the voltage multiplier 108 output is coupled to the variable-focus optic 112 through the H-bridge switch circuit 110, a circuit type widely known in the art. The H-bridge 110 comprises switches between the voltage multiplier 108 output and each of the variable-focus optic 112 terminals and between each of the variable-focus optic 112 terminals and an electrical ground of the system. The state of the H-bridge 110 is determined by one or more of the system controller 104 control signals applied to the H-bridge controller 106. The H-bridge controller 106 acts to interface the H-bridge 110 to the system controller 104. Generally, an H-bridge controller 106 will level-shift the control signals from a low-voltage digital controller, for example, system controller 104, which runs at a typical voltage of 1.8 volts, to the high-voltage H-bridge 110. The H-bridge controller 106 may also include timing and delay circuitry, circuitry to manage outputs to the H-bridge 110 with fewer inputs from the system controller 104, and circuitry to prevent problematic states in the H-bridge 110 such as shoot-through, a short-circuit condition known in the relevant art. The H-bridge 110 may be configured into one or more states such as with the lens terminals open, shorted to ground, or powered with one terminal coupled to the voltage multiplier 108 output and the other to ground, or powered in the opposite polarity. The H-bridge 110 provides a convenient method to energize the variable-focus optic 112 for actuation, discharge the variable-focus optic 112 to return it to a base power, and toggle the polarity of bias provided to the variable-focus optic 112. Grounding both terminals of the variable-focus optic allows charge in the optic 112 to be quickly removed, thereby allowing the variable-focus optic 112 to quickly change to the unenergized focus state instead of suffering a long delay as charge slowly dissipates through a high-isolation system. The system controller 104 may periodically reverse the polarity of the H-bridge 110 output to optimize the performance of the variable-focus optic 112, for example, to avoid excessive charge trapping that may occur when powered in one state for too long. It is important to note that the functional block are shown and described for illustrative purposes only, and that functional blocks may be added, removed or substituted while still relying on the basic principles of a lens driver designed and configured specifically for use in an electronic or powered ophthalmic device as described herein.

Figure 2:
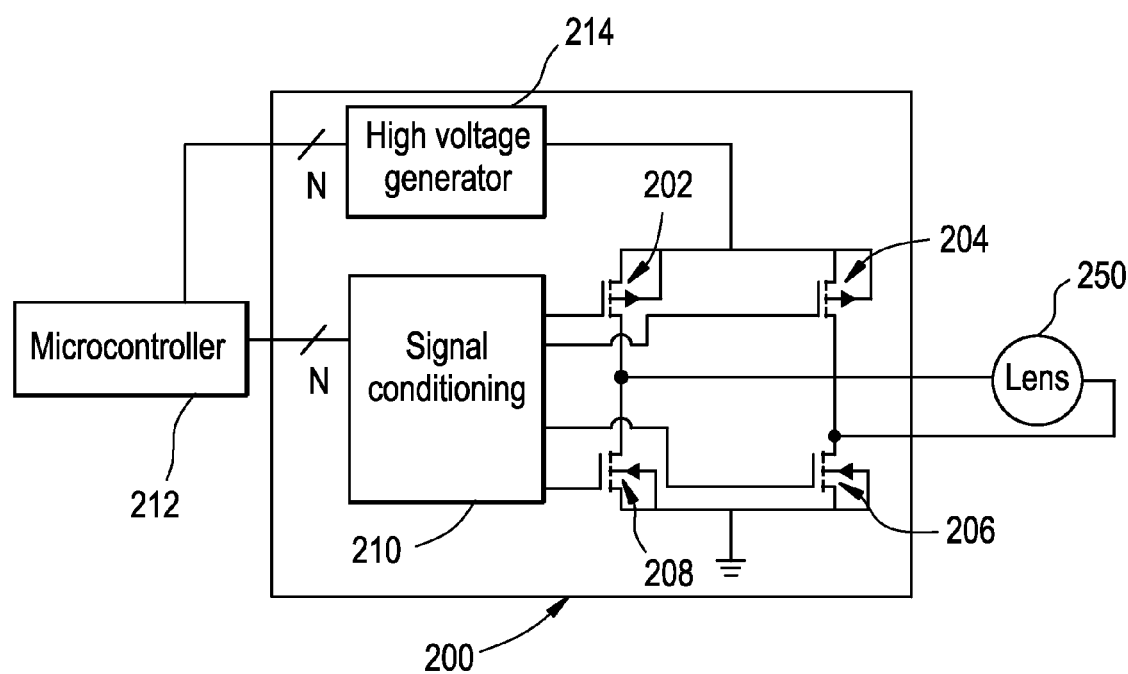
FIG. 2 is a diagrammatic representation of an exemplary H-bridge circuit coupled to a powered contact lens having a variable-focus optic in accordance with the present invention.

FIG. 2 illustrates an exemplary H-bridge circuit 200 coupled to a powered ophthalmic lens having a variable-focus optic 250. The H-bridge circuit 200 is particularly useful for controlling the voltage potential applied to the variable-focus optic 250 and may be used to switch voltage to the variable-focus optic 250, reverse polarity across the variable-focus optic 250, and ground the variable-focus optic 250. The exemplary H-bridge 200 comprises metal-oxide-semiconductor field-effect transistor or MOSFET switches 202, 204, 206 and 208 which are controlled by a signal conditioning circuit 210 and microcontroller 212. In the exemplary embodiment illustrated in FIG. 2, the microcontroller 212 corresponds to the system controller 104, and the signal conditioning circuit 210 corresponds to the H-bridge controller 106 as illustrated in FIG. 1. The microcontroller 212 could be replaced by a state machine or other device capable of controlling the lens driver circuitry. The signal conditioning circuit 210 is the interface between the microcontroller 212 and the H-bridge, for example, shifting voltage from a 1.8 V logic level to the gate drive needed for a 25 V output. It is important to note that the low voltage logic level may be as low as about 0.9 volts and the high level gate drive voltages may vary between 13 to 60 volts. It will be apparent to those skilled in the art that unique requirements exist for the voltages applied to the gates of the MOSFET switches 202, 204, 206 and 208 forming the H-bridge. Put another way, the low-level output voltages from a typical system controller are insufficient to turn off the high-side switches 202 and 204. The signal conditioning circuit 210 is also necessary to optimize current consumption by ensuring no two switches on the same leg (202 and 208, or 204 and 206) are closed at the same time. The variable-focus optic 250 connects to the outputs of the H-bridge. The H-bridge inputs connect to the high voltage generator 214 and to ground. The high voltage generator 214 may be a voltage multiplier, charge pump, or other circuit. Additional circuitry (not illustrated) may be required for implementation and control of the H-bridge 110 depending on the requirements thereof and the technology utilized for implementation thereof. For example, additional switches may be required depending on the high-voltage generator output level and the bias voltages available in the system.

In typical operation, one side of the variable-focus optic 250 will be connected to ground while the other side is connected to the high voltage generator 214. To accomplish this, the switches 202, 204, 206 and 208 forming the H-bridge are activated in the correct on/off combination. For example, if switches 202 and 206 are closed while switches 204 and 208 are open, the left side of the variable-focus optic 250 will connect to the high voltage generator 214 and the right side of the variable-focus optic 250 will connect to ground. This represents one case where the variable-focus optic 250 may be charged and thus activated. To deactivate the variable-focus optic 250, switches 202 and 204 are set open while switches 208 and 206 are closed. This eliminates any voltage potential across the variable-focus optic 250, which causes it to deactivate. Another potentially useful state is to apply a potential across the variable-focus optic 250, allow the variable-focus optic 250 to accumulate charge, then disconnect the variable-focus optic 250 and allow it to remain activated on stored charge only. This may be implemented by opening all switches 202, 204, 206 and 208 forming the H-bridge. Such a state may allow a further reduction in current consumption if the high voltage generator 214 is disabled while the variable-focus optic 250 is floating. Careful design of the variable-focus optic 250 capacitance and resistance, and leakage in the electronic system may allow the variable-focus optic 250 to store charge for many seconds, thereby greatly reducing the duty cycle of the high voltage generator 214 and hence the average current consumption.

Figure 3:
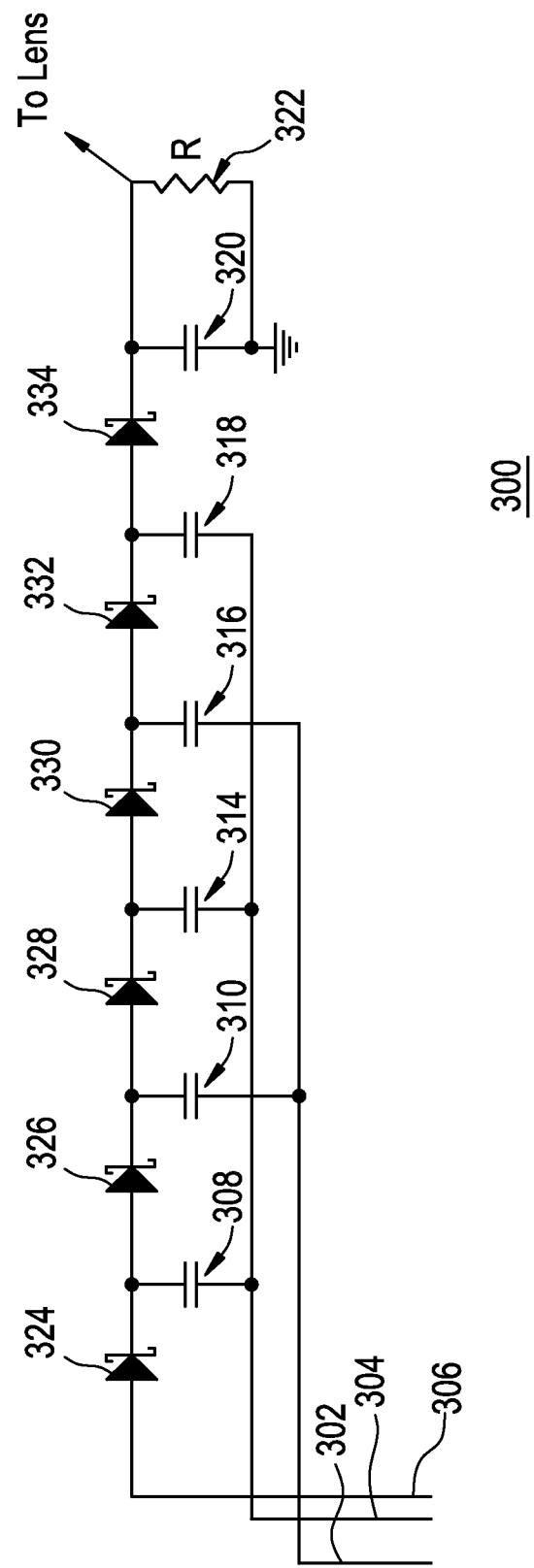
FIG. 3 is a diagrammatic representation of an exemplary diode-based charge pump lens drive in accordance with the present invention.
Figure 7:
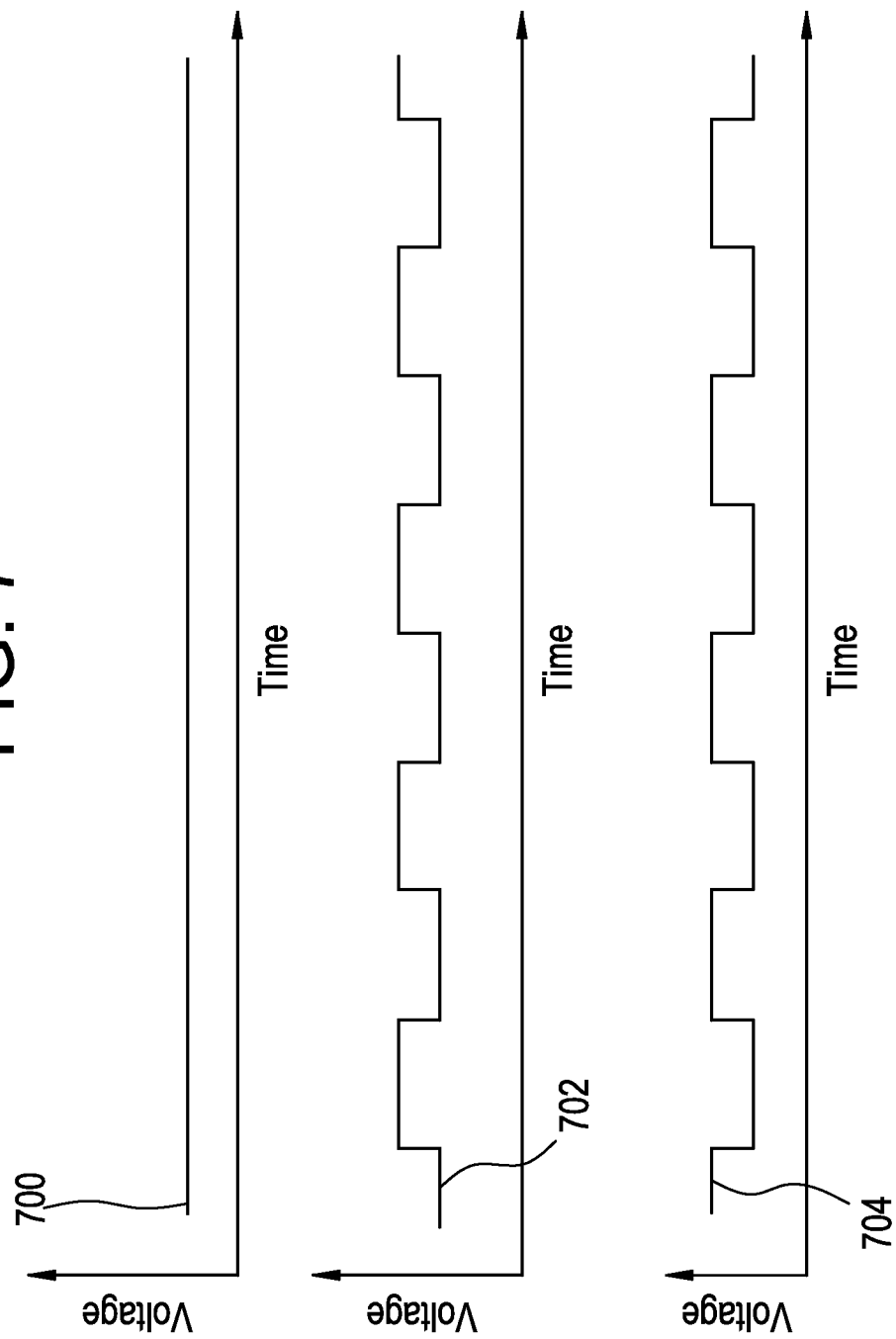
FIG. 7 is a graphical representation of input waveforms to an exemplary charge pump in accordance with the present invention.

FIG. 3 illustrates a diagrammatic representation of an exemplary diode-base charge pump lens driver 300. This particular configuration is known to those skilled in the relevant art as a Disckson Charge Pump. The diode-base charge pump or charge pump 300 is powered and controlled from inputs 302, 304, and 306. The input 306 is a constant DC voltage source which is continuously on when the charge pump 300 is active. When the DC voltage source is switched off, the charge pump 300 is inactive to save on current consumption. Inputs 304 and 302 are preferably square wave signals of complementary polarity which pulse during operation. FIG. 7 illustrates these signals. Inputs 302, 304, and 306 may be driven from a microcontroller, a hardware logic circuit or similar timing device, and typically have the same operating voltage as the control circuitry, for example 3.5 V. Capacitors 308, 314, and 318 form one side of the charge pump 300 and are connected to input 304. Capacitors 310 and 316 form the other side of the charge pump 300 and are controlled by input 302. Diodes 324, 326, 328, 330, 332, and 334 allow current to flow in only one direction, in this example, from left to right. A single stage of the charge pump 300 comprises a diode and the following capacitor, for example, 326 and 310. When voltage is applied to input 306, current flows through diode 324 and accumulates in capacitor 308. Initially, input 304 is low, so the voltage of capacitor 308 rises to equal that of input 306 less the forward voltage drop across diode 324. When input 304 rises, the voltage on the top plate of capacitor 308 increases. Current is unable to flow backward from capacitor 308 through diode 324 since the diode blocks reverse current. The charge from capacitor 308 passes through diode 326 and begins accumulating in capacitor 310. During this cycle, the bottom plate of capacitor 310 is low since input 302 is low. When the 304 and 302 inputs are toggled, the high voltage on input 302 causes the potential on the top plate of capacitor 310 to increase. This is repeated in subsequent stages, where the voltage increases in each stage by approximately the supply voltage minus the forward diode voltage drop. It will be appreciated that minimizing the voltage drop across the diodes increases the conversion efficiency of the charge pump; hence diodes with lower forward voltages, such as Schottky diodes, are typically utilized. Thus, at the output of the charge pump 300 into capacitor 320 and load resistor 322, the voltage present is roughly equal to the supply voltage (present on inputs 302, 304 and 306) multiplied by the number of stages, less forward diode voltage drops. In this implementation, with a supply voltage of 3.5 V the output voltage is approximately 21 V. Output capacitor 320 accumulates the charge from the last stage (capacitor 318 and diode 334). Load resistor 322 is provided to bleed charge off capacitor 320 and the load, in the event a known discharge time is required. A lens load is placed in parallel with capacitor 320 and load resistor 322. Thus, the lens receives a much higher voltage, approximately 21 V, than is possible with a direct drive from the microcontroller at approximately 3.5 V. It is important to note that this voltage may vary between 18 V and 20 V.

Figure 4:
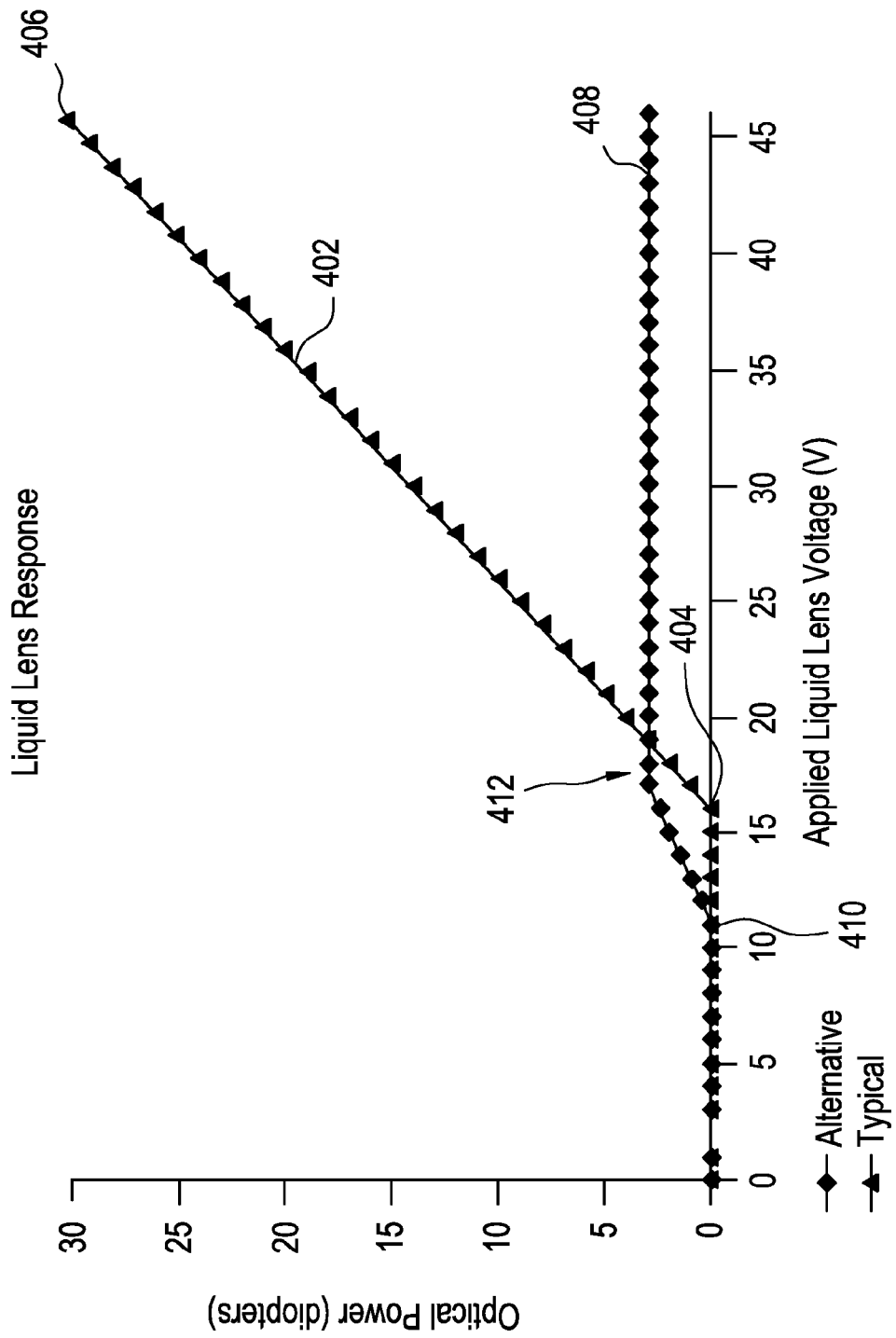
FIG. 4 is a graphical representation of an optical response for two variable-focus optics to applied voltage in accordance with the present invention.

FIG. 4 graphically illustrates a response of two variable-focus optics of two powered ophthalmic lenses to applied voltage across their terminals. In one exemplary design, a first variable-focus optic is a commercially available device comprising saline and oil with a substantially cylindrical shape. In a typical response 402 for this first lens, optical power of the variable-focus optic begins to increase once the applied voltage exceeds an activation voltage at a threshold reference point 404, in this example, approximately 16 V. It will be appreciated that this voltage is far in excess of that available from most single-cell battery chemistries. The first variable-focus optic has a linear response up to 46 V at endpoint reference 406. At low voltages up to the threshold reference point 404, the first variable-focus optic is in the deactivated state and possesses a baseline optical power. Above the threshold voltage, the first variable-focus optic's optical power increases. The threshold voltage and function of optical power versus applied voltage will vary depending on variable-focus optic design. A second lens design optimized for presbyopia correction is illustrated with function 408. In accordance with this exemplary design, the second variable-focus optic is a custom saline and oil optic with a substantially spherical shape. Essentially, this second variable-focus optic differs from the first one described above in saline and oil chemistry, dielectric material and mechanical design and hence the different response as described herein. This second variable focus-optic has a second threshold reference point 410 reduced to approximately 12 V, perhaps through optimizations to the variable-focus optic's fluid, mechanics, and dielectric thickness. Further optimizations of both the variable-focus optic and lens driver may be possible due to the unique storage and runtime characteristics of an ophthalmic device versus those of a commercially available electronic variable-focus optic, one which must run operate for many years with wide changes in focal length. The second variable-focus optic saturates at +3 diopters with approximately 17 V applied at reference point 412. Above this saturation voltage the variable-focus optic power is no longer variable with applied voltage. A design for a presbyopic and baseline myopitc patient may default to a negative optical power for distance vision correction. Other functions are possible based on the mechanical and chemical design of the variable-focus optic. It will be appreciated that above approximately 17 V, no change in optical power occurs. Correspondingly, a lens driver may be designed to reach 25 V with +/−8 V of potential error, and such a lens driver would still fully activate the second variable-focus optic, perhaps with no observable difference between 17 V and 33 V. Accordingly, the lens driver may be designed for imprecise control and substantial variation over input voltage, temperature, semiconductor, and other parameters. Such design tradeoffs allow the lens driver to be implemented with a simpler circuit, one that consumes less power and area.

Figure 5:
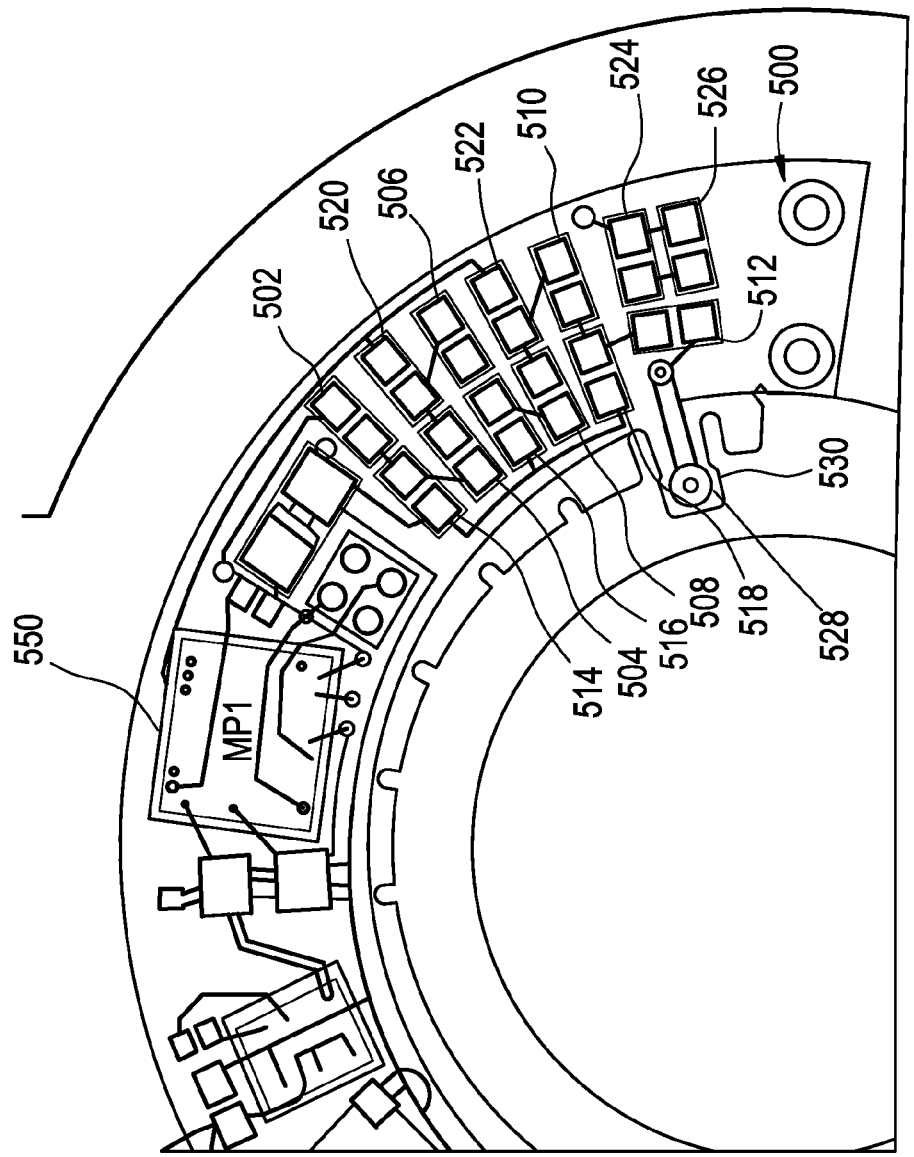
FIG. 5 is a diagrammatic representation of the layout of a discrete lens driver circuit on a circuit board in accordance with the present invention.

It will be appreciated that the lens driver may be implemented in either discrete or integrated form, with varying levels of integration possible. FIG. 5 illustrates the layout of devices for an exemplary discrete lens driver circuit in accordance with the present invention on a circuit board 500. The circuit board 500 is preferably cut into the shape of an annular ring, thereby permitting it to be formed into a conical section for incorporation into a lens, for example, a contact lens or an intraocular lens. A microcontroller 550 drives a charge pump depending on internal programming and the state of various sensors. As described with respect to FIG. 3, diodes 502, 504, 506, 508, 510 and 512 block the reverse flow of current and allow charge to pass from one stage to the next in the charge pump. Capacitors 520 and 522 connect to the 302 input (FIG. 3) whereas capacitors 514, 516, and 518, connect to the 304 input (FIG. 3). Load capacitor 524 and load resistor 526 are present in parallel with the lens driver output. A trace and via 528 connect the lens driver output to a tab 530 on the circuit board 500. This tab 530 bends into position and may be attached to one side of the lens with conductive epoxy.

Figure 6:
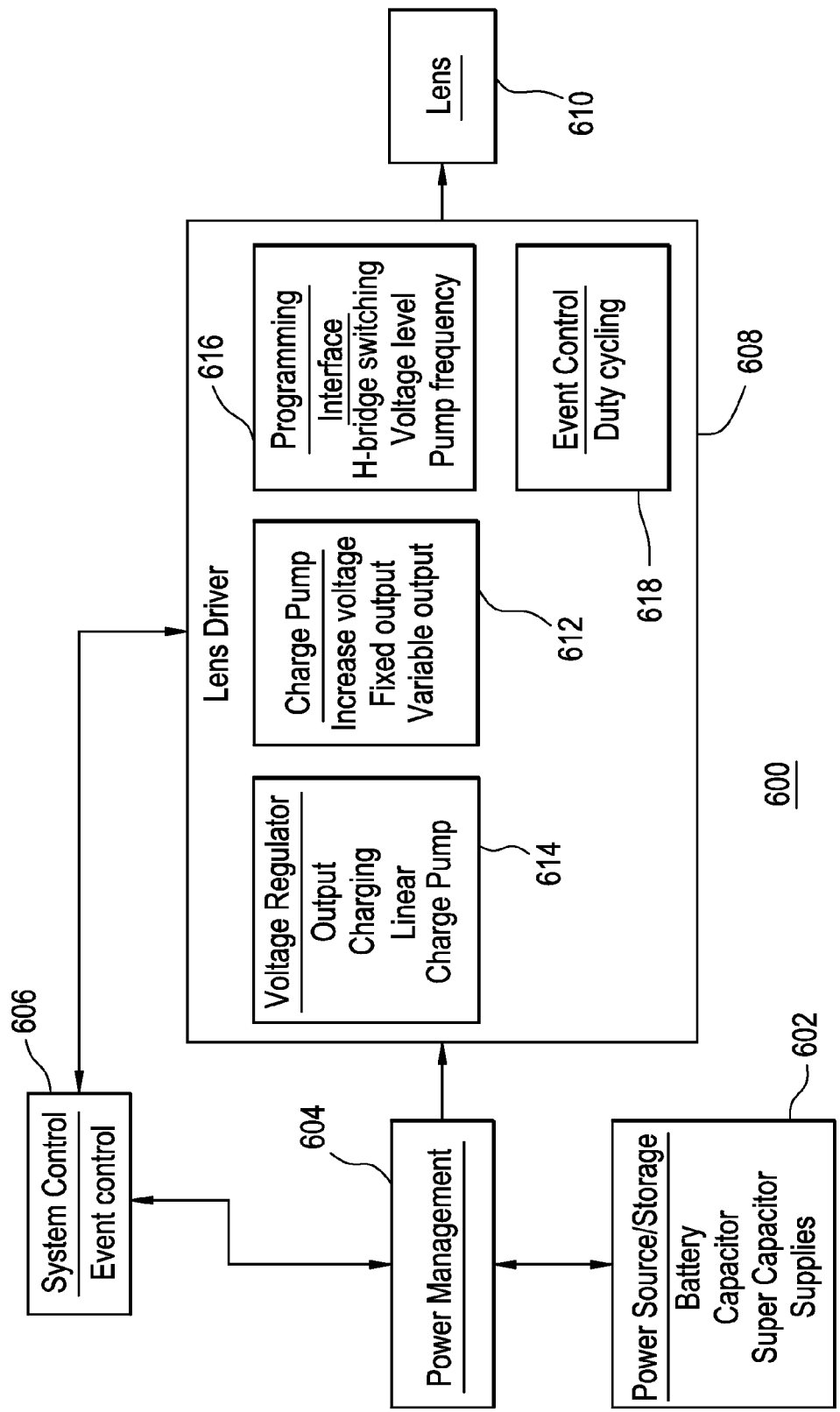
FIG. 6 is a block diagram representation of an exemplary lens driver-optics interface in accordance with the present invention.

Referring now to FIG. 6, system block diagram 600 illustrates how an exemplary lens driver interfaces with the electro-optical system. The exemplary system 600 comprises batteries 602 or any other suitable power source. For this application, the power source 602 is constrained for voltage and current by competing system requirements, for example, small size. The power source 602 is applied to a power management block 604 which may provide a regulated output, switch off the load at a defined battery cutoff threshold, allow for battery charging, and other suitable functions. A system control block 606 is responsible for event timing and activation. It may be implemented as a microcontroller, state machine, or other circuitry. The system control block 606 may include or interface with sensor circuitry to determine the desired variable-focus optic state. The lens driver 608 receives control signals from the system control block 606 and power from the power management block 604 or perhaps directly from the power source 602. A lens 610 connects to the lens driver 608. The lens driver 608 may comprise functions to increase voltage via a charge pump 612, regulate voltage via a voltage regulator 614, toggle polarity, ground the lens, float the lens, and the like via a programming interface and event control block 610 and 618 respectively.

FIG. 7 illustrates sample input waveforms to an exemplary charge pump 300 such as illustrated in FIG. 3. Waveform 700 is a constant DC voltage, for example 3.5 V from a battery. Signal 700 may be switched off when the charge pump is not in operation. Waveform 702 and 704 are complementary signals toggling between, for example, ground and 3.5 V. On one half-cycle, 702 is high while 704 is low. This causes one set of capacitors in the charge pump to charge. On the other half-cycle, 702 is low while 704 is high. This causes the other set of capacitors to charge. As each capacitor charges, a difference in voltage potential is created across the series diodes. The potential cannot create current flow towards the sources since the diodes prevent current flow in the reverse direction. The potential causes current to flow through the diodes toward the load. At each stage, the voltage is increased by approximately 3.5 V minus a loss factor.

Figure 8:
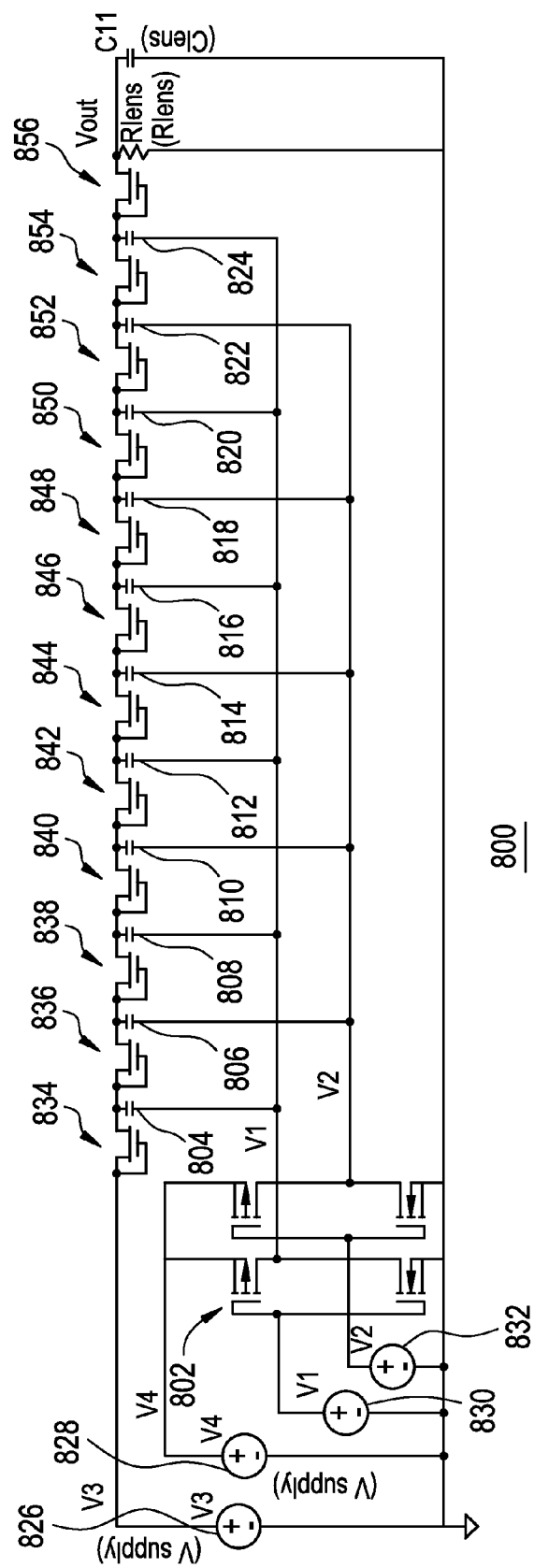
FIG. 8 is a diagrammatic representation of an alternate exemplary charge pump lens driver in accordance with the present invention.

FIG. 8 illustrates an alternate exemplary lens driver 800 using metal-oxide-semiconductor field-effect transistors (MOSFETs) connected as diodes instead of discrete diodes as was shown and described with respect to FIG. 3. This implementation is more common in integrated circuits, although other circuits are possible and may be utilized for the lens driver in accordance with the present invention and described herein. Clock inputs 830 and 832 represent the complementary signals which drive the charge pump capacitors; namely, 302 and 304 illustrated in FIGS. 3, and 702 and 704 illustrated in FIG. 7. A clock buffer stage 802 precludes the diodes and switches of the lens driver 800. Non-overlapping clocks are required to avoid shoot-through current in the switches and to ensure proper operation of the charge pump 800. In this figure, the non-overlapping clocks are defined in the simulation parameters. Those skilled in the art will appreciate that the clocks could be generated in a digital control block or with other non-overlapping clock generation circuitry known in the art. Supplies 826 and 828 represent the power supply input; namely, 306 illustrated in FIGS. 3 and 700 illustrated in FIG. 7. Capacitors 804, 806, 808, 810, 812, 814, 816, 818, 820, 822 and 824 are positioned between the MOSFETs 834, 836, 838, 840, 842, 844, 846, 848, 850, 852, 854 and 856. MOSFET switches 834-856 are illustrated as three terminal devices, understood to have their bulk terminals tied to ground. Additional circuitry is required to optimize operation of the charge pump 800 to account for non-idealities in the MOSFETS, for example, turn-on voltage and the body effect. For example, the MOSFET bulk terminals may be biased at higher voltages as voltage builds in the charge pump 800. In an appropriate circuit for the exemplary lens driver described herein, the MOSFETs would preferably be chosen appropriately from a library of devices in a special high-voltage semiconductor fabrication process. For example, such MOSFETs preferably have gate oxide and drain-source breakdown voltages sufficiently high to withstand the voltages created by the charge pump, as high as sixty (60) volts or more at the output. Standard devices used in typical complementary metal-oxide semiconductor (CMOS) processes would not have sufficient breakdown voltage capability for this exemplary lens driver. Accordingly, due to the use of high voltages and high-voltage MOSFETs, the driving waveforms, including perhaps the gate and well biasing, must be appropriate for the circuit described. Although high-voltage, foundry-specific device models and driving circuitry are not shown in this illustration, those knowledgeable in the field will recognize the need to design appropriately with these devices.

Figure 9:
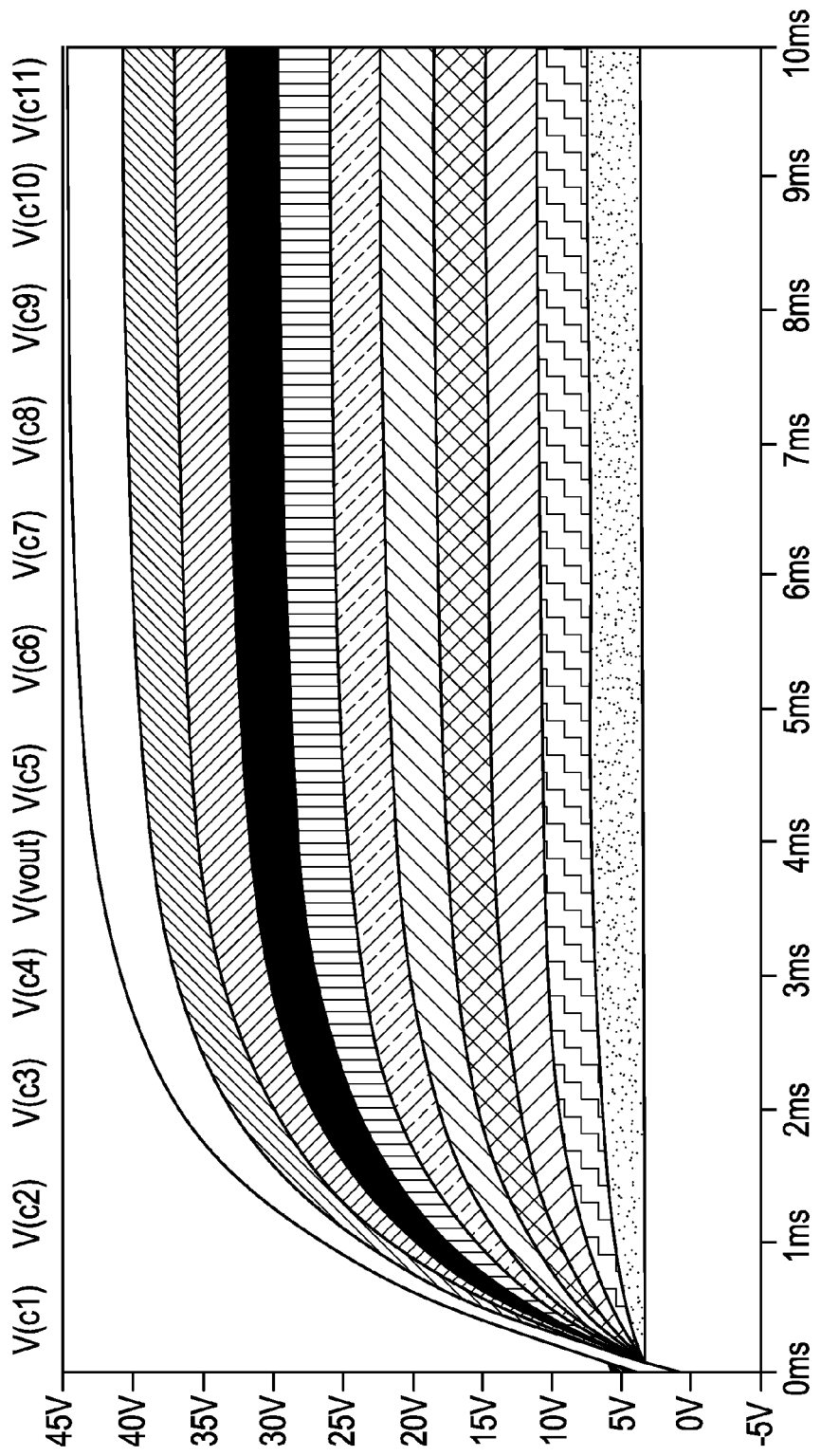
FIG. 9 is a graphical representation of a simulation of voltage versus time at each capacitor's top plate node in the exemplary charge pump of FIG. 8.

FIG. 9 shows simulated voltage versus time at each capacitor's top plate node in the exemplary system of FIG. 8 along with the final output voltage. In this example or simulation, the lens driver charges the load to approximately 43 V in ten (10) milliseconds. The load is two (2) gigaohms in parallel with one-hundred (100) picofarads, a model of the lens developed from laboratory measurements. The schematic shown in FIG. 8 was operated at a clock frequency of 1 kHz with 1 pF for each stage's capacitor.

Figure 10:
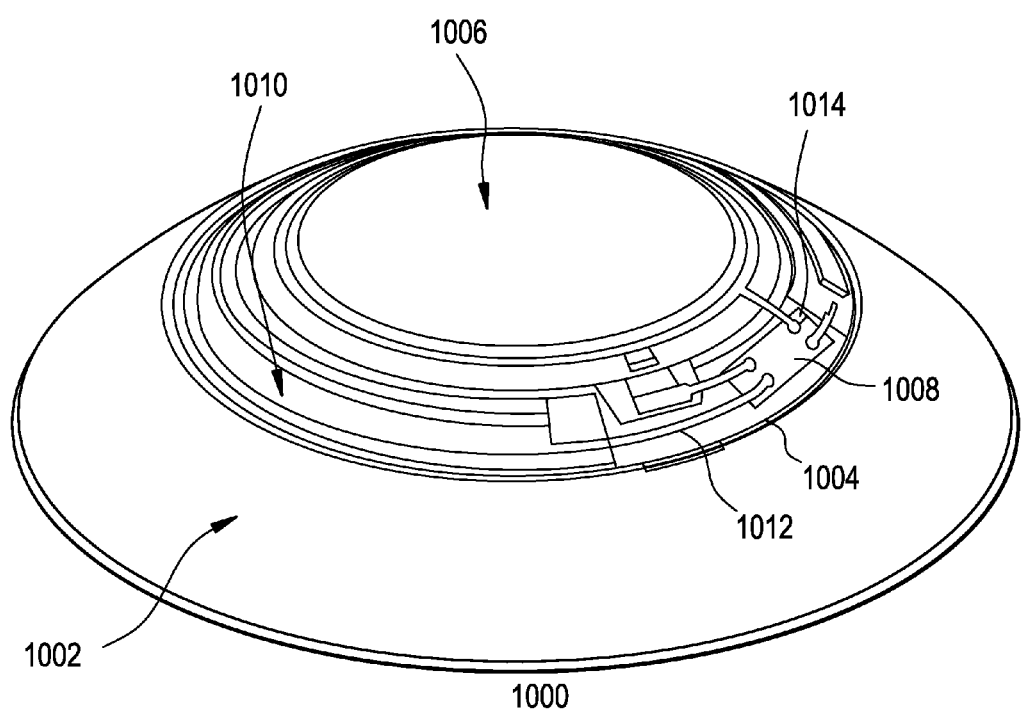
FIG. 10 is a diagrammatic representation of an exemplary electronic insert, including a lens driver, for a powered contact lens in accordance with the present invention.

Referring now to FIG. 10, there is illustrated an exemplary contact lens with an electronic insert comprising the lens driver in accordance with exemplary embodiments of the present invention. The exemplary contact lens 1000 comprises a soft plastic portion 1002 which comprises an electronic insert 1004. This electronic insert 1004 includes a lens 1006 which is activated or controlled by the electronics described herein, for example, focusing near or far depending up activation. Circuitry 1008 mounts onto the insert 1004 and is connected to a power source 1010, such as batteries via one or more electrical interconnect traces 1012. Additional circuitry may also be connected via the electrical interconnect traces 1012. Circuitry 1008 may include any of the components set forth herein, including one or more sensors 1014.

Those of ordinary skill in the art will recognize that further embodiments and variations of the variable-focus lens system are possible. The input to the voltage multiplier may be coupled directly to the power source or it may be coupled to the output of a voltage regulator. The system may comprise an H-bridge to provide flexible control of the lens terminal voltages, or the system may comprise only a simple switch to one terminal with the other terminal grounded, or it may comprise no switches with the lens always coupled in one way to the voltage multiplier output. Each variation may provide a different tradeoff between system cost, area and performance or efficiency.

In one exemplary embodiment, the electronics and electronic interconnections are made in the peripheral zone of a contact lens rather than in the optic zone. In accordance with an alternate exemplary embodiment, it is important to note that the positioning of the electronics need not be limited to the peripheral zone of the contact lens. All of the electronic components described herein may be fabricated utilizing thin-film technology and/or transparent materials. If these technologies are utilized, the electronic components may be placed in any suitable location as long as they are compatible with the optics.

It is important to note that the circuitry described herein may be implemented in hardware, software or a combination of hardware and software. In addition, the circuit board utilized herein may comprise any suitable substrate, including copper traces on a flexible polyimide substrate with a nickel-gold surface finish.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An ophthalmic apparatus comprising:
    an ophthalmic device configured for use in at least one of in or on the eye;
    an optic element incorporated into the ophthalmic device, the optic element having an electronically controlled focal length configurable for at least one of vision correction and vision enhancement; and
    an electronic system incorporated into the ophthalmic device, the electronic system comprises on or more power sources, a power management device for regulating the output of the one or more power sources, a system controller and a lens driver, the system controller receiving power from the power management device and providing control and timing signals thereto and receiving feedback signals from the lens driver, the lens driver receiving a regulated power output from the power management device and control and timing signals from the system controller, the lens driver comprising a voltage regulator, a charge pump to increase the voltage from the voltage regulator, an H-bridge circuit configured to control the voltage potential to the optic element, reverse the polarity of the voltage potential to the optic element and to ground the optic element, and a control device.

2. The ophthalmic apparatus according to claim 1, wherein the ophthalmic device comprises a contact lens.

3. The ophthalmic apparatus according to claim 2, wherein the contact lens comprises a soft contact lens.

4. The ophthalmic apparatus according to claim 2, wherein the contact lens comprises a hybrid soft/rigid contact lens.

5. The ophthalmic apparatus according to claim 1, wherein the ophthalmic device comprises an intraocular lens.

6. The ophthalmic apparatus according to claim 1, wherein the optic element operates in one of two focal lengths.

7. The ophthalmic apparatus according to claim 1, wherein the electronic system is implemented on an integrated circuit.

8. The ophthalmic apparatus according to claim 1, wherein the optic element comprises a liquid meniscus lens.

9. The ophthalmic apparatus according to claim 1, wherein the one or more power sources comprise a battery.

10. The ophthalmic apparatus according to claim 7, wherein the integrated circuit is incorporated onto a circuit board.

11. The ophthalmic apparatus according to claim 10, wherein the circuit board is configured as an annular ring and formed into a conical section for incorporation into a contact lens.

12. The ophthalmic apparatus according to claim 10, wherein the circuit board is configured as an annular ring and formed into a conical section for incorporation into an intraocular lens.

13. The ophthalmic apparatus according to claim 10, wherein the circuit board comprises at least one of a polymer or plastic insert with metalized traces.

* * * * *